United States Patent [19]

Bowman et al.

[11] Patent Number: 5,256,786

[45] Date of Patent: Oct. 26, 1993

US005256786A

[54] CATALYTIC REFORMING OF CYCLIC ALKYLENEAMINES

[75] Inventors: Robert G. Bowman; David C. Molzahn; George E. Hartwell, all of Midland, Mich.

[73] Assignee: The Dow Chemical Company, Midland, Mich.

[21] Appl. No.: 844,816

[22] Filed: Mar. 2, 1992

[51] Int. Cl.$^5$ .............. C07D 295/023; C07D 295/13; C07C 209/16; C07C 209/64

[52] U.S. Cl. ..................... 544/402; 544/357; 544/358; 544/401; 564/469; 564/470; 564/478; 564/479; 564/480; 564/512

[58] Field of Search .............. 544/357, 401, 382, 383, 544/402, 358; 564/429, 480, 469, 470, 479, 512, 480, 478

[56] References Cited

U.S. PATENT DOCUMENTS

| | | | |
|---|---|---|---|
| 2,474,781 | 6/1949 | Dixon. | |
| 2,716,134 | 8/1955 | Reynolds et al. | 546/186 |
| 3,565,837 | 2/1971 | Drawert et al. | 540/612 |
| 3,903,079 | 9/1975 | Heinz et al. | 544/404 |
| 3,956,329 | 5/1976 | Murakami et al. | 544/404 |
| 4,105,657 | 8/1978 | Dockner et al. | 544/402 |
| 4,316,840 | 2/1982 | Ford et al. | 544/402 |
| 4,547,591 | 10/1985 | Brennan et al. | 564/479 |
| 4,552,961 | 11/1985 | Herdle | 544/402 |
| 4,793,569 | 12/1988 | Ohsaki | 242/195 |
| 4,927,931 | 5/1990 | Molzahn et al. | 544/357 |
| 4,983,735 | 1/1991 | Hartwell et al. | 544/402 |
| 4,996,363 | 2/1991 | Bowman et al. | 544/358 |
| 5,011,999 | 4/1991 | Bowman et al. | 564/479 |
| 5,030,740 | 7/1991 | Bowman et al. | 544/357 |
| 5,073,635 | 12/1991 | Bowman et al. | 544/357 |

OTHER PUBLICATIONS

Anderson et al., *Bulletin of the Academy of Sci. of Latvian SSR*, Chemical Series 1971, Nr. 1, 47-58.

Anderson et al., *Doklady Akademii Nauk SSSR*, 1966, vol. 169, Nr. 6, 1332-1334.

Chemical Abstracts 82:156378h.

*Primary Examiner*—Cecilia Tsang

[57] ABSTRACT

A process of reforming cyclic alkyleneamines to amine-extended cyclic alkyleneamines involving contacting a cyclic alkyleneamine or mixture of cyclic alkyleneamines in the liquid phase with a catalyst under reaction conditions. The catalyst is selected from the group consisting of (a) Group VB metal oxides, (b) Group VB metal phosphates, (c) silicates of Groups IIA, IIIB, IVB and VB, and (d) specified tungsten oxides. For example, piperazine or a mixture of piperazine and aminoethylpiperazine is contacted with magnesium silicate to yield a mixture of amine-extended piperazines, including 1,2-bis(piperazinyl)-ethane and N,N'-bis(2-piperazinylethyl)piperazine.

30 Claims, No Drawings

CATALYTIC REFORMING OF CYCLIC ALKYLENEAMINES

BACKGROUND OF THE INVENTION

This invention relates to a process of reforming cyclic alkyleneamines to amine-extended cyclic alkyleneamines. Examples of amine-extended cyclic alkyleneamines include bis(piperazinyl)alkanes, bis(piperidinyl)alkanes, (aminoalkyl)bis(piperazinyl) alkanes, and higher homologues of these compounds, such as tris(piperazinyl)-alkanes and (aminoalkyl)tris(piperazinyl)alkanes.

Amine-extended cyclic alkyleneamines are useful as dispersants, surfactants, chelants, catalysts, curing agents, extenders in polyurethanes, and as starting materials in the preparation of pesticides.

It is known that bis(piperazinyl)alkanes and bis(piperidinyl)alkanes can be prepared by the reaction of an alkyl dihalide with piperazine or piperidine, respectively. The reaction yields the corresponding hydrohalide salts which must be neutralized with base in order to recover the valuable bis(piperazinyl)alkane and bis(piperidinyl)alkane products. Disadvantageously, the neutralization produces a waste stream of metal salt which must be removed.

Other organic syntheses of bis(piperazinyl)alkanes and bis(piperidinyl)alkanes are known. For example, U.S. Pat. No. 2,716,134 discloses the preparation of N,N'-bis(piperidinyl)pentane comprising reacting piperidine with 1,5-di(methanesulfoxy)pentane. Disadvantageously, the sulfoxy-containing reactant is difficult to obtain, and the products do not include any higher homologues of N,N'-bis(piperidinyl)pentane.

Direct catalytic methods of preparing amine-extended cyclic alkyleneamines are also known. For example, U.S. Pat. No. 4,552,961 discloses a process for the preparation of polyalkylene polypiperazines comprising reacting piperazine or aminoethylpiperazine with alkanolamines or alkylene glycols in the presence of a phosphorus amide catalyst. Disadvantageously, this catalyst is homogeneous and must be separated from the product stream. In addition, the process generates water as a by-product which must be separated from the polypiperazine products.

Typically, direct catalytic methods involving cyclic alkyleneamines tend to yield undesirable products from internal cyclization, cracking, and dehydrogenation. For example, U.S. Pat. No. 3,956,329 discloses contacting N-(2-aminoethyl)piperazine with a catalyst comprising an aluminosilicate zeolite of the formula:

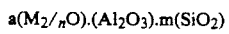

$$a(M_{2/n}O).(Al_2O_3).m(SiO_2)$$

wherein M represents a cation selected from alkali metals, alkaline earth metals, zinc group elements, and hydrogen and ammonium cations; "n" represents the valence of the cation, "a" represents $1.0\pm0.5$ regardless of the type and number of the cation, and "m" represents the numbers 2 to 12. Disadvantageously, this process produces large quantities of internal cyclization and cracking products, such as triethylenediamine and piperazine.

U.S. Pat. No. 2,474,781 discloses contacting piperazine in the vapor phase at an elevated temperature with a catalyst comprising a Group VB or VIB oxide, such as vanadium oxide or tungsten oxide, supported on alumina. Disadvantageously, the products include large quantities of dehydrogenation products, such as pyrazine.

Similarly, the vapor phase deamination of N-(2-aminoethyl)piperazine at 400° C. over a kaolin catalyst is reported by A. A. Anderson et al. in Doklady Akademii Nauk SSSR, 169 (6), (1966), 1332-1334, to yield cracking products, such as ethylenediamine and piperazine; dehydrogenation products, such as pyrazine; and internal cyclization products, such as triethylenediamine.

Among the different processes reported in the prior art, none appears to be selective to amine-extended cyclic alkyleneamines and also suitable for commercial application. It would be desirable to find an inexpensive catalyst which is capable of reforming cyclic alkyleneamines directly to amine-extended cyclic alkyleneamines. It would be more desirable if such a process produced high yields of amine-extended cyclic alkyleneamines and simultaneously low yields of cracking products, dehydrogenation products, and internal cyclization products. It would be even more desirable if the catalyst for such a process was insoluble in amines and water, so as to avoid catalyst losses and separation problems.

SUMMARY OF THE INVENTION

This invention is a process of reforming cyclic alkyleneamines to amine-extended cyclic alkyleneamines. The process comprises contacting in the liquid phase a cyclic alkyleneamine or mixture of cyclic alkyleneamines with a catalyst, described hereinafter, under reaction conditions such that at least one amine-extended cyclic alkyleneamine is produced. The catalyst is selected from the group consisting of:

(a) Group VB metal oxides;
(b) Group VB metal phosphates;
(c) metal silicates wherein the metal is selected from Groups IIA, IIIB, IVB and VB of the Periodic Table, with the proviso that the metal silicate is essentially free of aluminum; and
(d) binary compounds of tungsten and oxygen and salts thereof, as well as binary compounds of tungsten and oxygen wherein a portion of the tungsten atoms are replaced by vanadium, niobium, or tantalum.

Advantageously, the process of this invention converts cyclic alkyleneamines directly to amine-extended cyclic alkyleneamines. Accordingly, the process of this invention does not require the neutralization of hydrohalide salts, the disposal of a waste metal salt stream, or the presence of expensive specialty organic reagents. More advantageously, the process of this invention does not produce water as a by-product. Even more advantageously, the catalysts of this process are insoluble in water and amines. Consequently, catalyst losses are minimized, and the separation of products from the catalyst is relatively easy should water be present in the feedstream or as a solvent. Most advantageously, the process of this invention can be controlled to give high selectivities to amine-extended cyclic alkyleneamines, including higher oligomers. Simultaneously, the process produces low selectivities to undesirable cracking products, dehydrogenation products and internal cyclization products of low value.

The amine-extended cyclic alkyleneamine products of this invention are useful as dispersants, surfactants, curing agents, chelants, and catalysts, and are further useful in the production of urethane polymers, ureas, and pesticides.

DETAILED DESCRIPTION OF THE INVENTION

As noted hereinabove, the products of the process of this invention are amine-extended cyclic alkyleneamines. These products are described in detail hereinafter, but are easily illustrated by the following compounds or mixtures. The first is a mixture comprising (piperazinylethyl)ethylenediamine, 1,2-bis(piperazinyl)ethane, and N-(2-aminoethyl)piperazine. These compounds are amine-extended piperazines prepared in the process of this invention by reacting piperazine with itself. As a second example, 1,2-bis(-piperazinyl)ethane may also be prepared in the process of this invention by reacting piperazine with N-(2-aminoethyl)piperazine. A third example comprises a mixture of 1,5-bis(piperidinyl)pentane and N-(5-aminopentyl)piperidine. These are amine-extended piperidines which may be prepared in the process of this invention by reacting piperidine with itself. It is observed that in each example the products are amine-extended cyclic alkyleneamines obtained by reforming a cyclic alkyleneamine with itself or with a second reactant amine which may be cyclic or acyclic.

The cyclic alkyleneamine reactants, which can be reformed in the process of this invention, are characterized as saturated heterocyclic ring systems containing nitrogen. Typically, these are four, five, six, seven or eight-membered ring systems containing one or at most two nitrogen atoms. Preferably, the ring system is five or six-membered with one or two nitrogen atoms. Non-limiting examples of suitable saturated N-heterocycles include piperazine, piperidine, pyrrolidine, imidazolidine, pyrazolidine, and morpholine. Certain partially unsaturated N-heterocycles are also suitable for the process of this invention, provided that at least one saturated carbon atom is adjacent to the nitrogen of the ring system. Such partially unsaturated N-heterocycles include pyrroline, imidazoline and pyrazoline. In addition, certain fused ring systems wherein the N-heterocycle is fused to a benzene ring are acceptable, such as indoline and isoindoline. Aromatic or conjugated N-heterocycles, such as pyrrole, imidazole, pyrazole, pyridine, pyrazine, purine and quinoxaline are not intended for the process of this invention.

Substituted derivatives of the aforementioned saturated N-heterocycles, preferably alkyleneamine-substituted derivatives, are also suitable reactants for the process of this invention. Non-limiting examples include alkylamine-substituted piperazines, such as, N-(2-aminoethyl)piperazine, N,N'-bis(2-aminoethyl)piperazine, N-(3-aminopropyl)piperazine, N,N'-bis(3-aminopropyl)piperazine; alkylamine-substituted piperidines, such as, N-(2-aminoethyl)piperidine and N-(3-aminopropyl)piperidine; alkylamine-substituted morpholines, such as N-(2-aminoethyl)morpholine and N-(3-aminopropyl)morpholine; bis(piperazinyl)alkanes, such as bis(piperazinyl)ethane and bis(piperazinyl)propane; tris(piperazinyl)alkanes, such as N,N'-bis(2-piperazinylethyl)piperazine; and analogous oligo(piperazinyl)alkanes; as well as aminoalkyl-substituted pyrrolidines, imidazolidines and pyrazolidines, such as N-(2-aminoethyl)pyrrolidine, N-(2-aminopropyl)imidazolidine, and N-(2-aminobutyl)pyrazolidine.

Mixtures of cyclic alkyleneamines, including mixtures of any of the aforementioned examples, may also be employed in the process of this invention. While the above-identified cyclic alkyleneamines are representative of those which are known to be suitable for the process of this invention, other cyclic alkyleneamines may be found which are equally suitable.

The preferred cyclic alkyleneamines can be represented by the general formula:

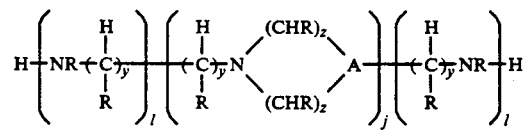

wherein A is either N or CH, each R is independently hydrogen, an alkyl moiety of $C_1-C_{12}$ carbon atoms, such as methyl, ethyl or propyl; or an aminoalkyl moiety of $C_1-C_{12}$ carbon atoms; each y is independently an integer from 0 to about 12; each z is independently an integer from 1 to 3; each l is independently an integer from 0 to about 6; and j is an integer from 1 to about 6. Some examples of reactant amines which satisfy this formula include piperazine, piperadine, N-(2-aminoethyl)piperazine, N,N'-bis(2-aminoethyl)piperazine, 1,2-bis(piperazinyl)ethane, and N-(2-aminoethyl)bis(piperazinyl)ethane. Preferably, each R is hydrogen. More preferably, each R is hydrogen, y is 0 to 2, z is 2, j is 1 or 2, and l is 0 to 2. Most preferably, each R is hydrogen, A is nitrogen, y is 0, z is 2, j is 1, each l is 0, and the compound is piperazine.

Optionally, other reactant amines can be combined with one or more of the above-identified cyclic alkyleneamines to form mixtures which are suitable starting materials for the process of this invention. The optional reactant amines include ammonia and acyclic primary or secondary alkyl amines, including simple alkyl monoamines, such as methylamine, dimethylamine, ethylamine, diethylamine, propylamine, dipropylamine, and the like; alkylene diamines, such as 1,2-ethylenediamine, 1,3-propylenediamine, 1,4-butylenediamine, 1,5-pentamethylenediamine, 1,6-hexamethylenediamine and the like; polyalkylenepolyamines, such as diethylenetriamine, linear and branched triethylenetetramines, linear and branched tetraethylenepentamines, and analogous higher homologs of ethylenepolyamines and propylenepolyamines; as well as polyether alkyleneamines such as 2-($\beta$-aminoethoxy)aminoethane, 1,4-bis($\beta$-aminoethoxy)butane, and 1,4-bis($\gamma$-aminopropoxy)butane.

Although it is preferred to carry out the amination reaction in the absence of solvent, it is within the scope of the invention for a solvent to be used, if desired. Any solvent is acceptable provided that (1) it is not reactive with the cyclic and acyclic alkyleneamine reactants or amine-extended cyclic alkyleneamine products, and (2) it does not decompose under the conditions of the reaction. Some examples of suitable solvents include saturated aliphatic hydrocarbons, such as pentane, hexane, octane, nonane, and decane; and aromatic hydrocarbons, such as benzene, toluene, and xylene. The amount of solvent employed in the reaction depends upon the particular reactants and reaction conditions. Any amount of solvent is acceptable that meets the intended purpose of use. Typically, the solvent constitutes from about 5 weight percent to about 95 weight percent of the feedstream. Preferably, the solvent constitutes from about 10 weight percent to about 80 weight percent of the feedstream.

It is not desirable for the reaction mixture in the process of this invention to contain alcohols capable of reacting with the cyclic alkyleneamine feedstock or amine-extended cyclic alkyleneamine products. Such alcohols would condense with the cyclic alkyleneamines to yield alkyl-extended cyclic alkyleneamines, and water would be formed as a by-product. The process of this invention is not intended to embrace alcohol-amine condensation reactions, therefore, alcohols with such a reactive capability should be excluded from the process of this invention.

A variety of catalysts can be employed in the reforming process of this invention including (a) Group VB metal oxides, (b) Group VB metal phosphates, (c) metal silicates wherein the metal is selected from Groups IIA, IIIB, IVB and VB of the Periodic Table with the proviso that the metal silicate is essentially free of aluminum, and (d) binary compounds of tungsten and oxygen and salts thereof, and binary compounds of tungsten and oxygen wherein a portion of the tungsten atoms are replaced by vanadium, niobium or tantalum. These catalysts can be employed in the reforming process singly or in mixtures with each other. A detailed description of each catalyst group is given hereinbelow.

A. Group VB Metal Oxides

Group VB metal oxides are suitably employed as catalysts in the reforming process of this invention. The Group VB elements include vanadium (V), niobium (Nb), and tantalum (Ta). Examples of suitable Group VB metal oxides include vanadium oxides such as VO, $VO_2$, $V_2O_3$, $V_2O_5$, $V_3O_5$, $V_5O_9$, $V_6O_{13}$; niobium oxides such as NbO, $NbO_2$, $Nb_2O_5$; tantalum oxides such as $Ta_2O_5$; as well as hydrated oxides including vanadates such as $H_3VO_4$, niobic acids such as $Nb_2O_5.xH_2O$, $H_8Nb_6O_{19}.xH_2O$, and $[H_2Nb_6O_{16}]_m$, tantalic acid, and mixtures of Group VB metal oxides and/or hydrated metal oxides. Non-stoichiometric oxides are also suitable. Preferably, the Group VB metal oxide is an oxide or hydrated oxide of niobium. More preferably, the Group VB metal oxide is a hydrated niobium oxide.

Generally, the common Group VB metal oxides are commercially available; while the less common oxides can be prepared by methods known in the art. The preparation of some less common Group VB metal oxides can be found in *Comprehensive Inorganic Chemistry*, Vols. 1-5, J. C. Bailar, Jr., H. J. Emeleus, R. Nyholm, and A. F. Trotman-Dickenson, eds., Pergamon Press, Oxford (1973) pp. 510-524 and 592-599, and the references cited therein.

B. Group VB Metal Phosphates

A Group VB metal phosphate can also be suitably employed as a catalyst in the reforming process of this invention. As noted hereinabove, the Group VB metals include vanadium, niobium, and tantalum. Examples of suitable Group VB metal phosphate compounds include vanadium phosphates such as $V_2O_5.P_2O_5$; niobium phosphates such as $2Nb_2O_5.P_2O_5.6H_2O$, $2Nb_2O_5.P_2O_5$, $NbOPO_4$, $PNb_9O_{25}$; and tantalum phosphates such as $2Ta_2O_5.P_2O_5$, $2Ta_2O_5.P_2O_56H_2O$, $TaOPO_4$. Group VB metal meta-phosphates, fluorophosphates, hydrated phosphates, and non-stoichiometric phosphate compounds are also suitable, as are Group VB metal hydrogen phosphates. Preferably, the Group VB metal phosphate possesses a P/metal mole ratio no greater than about 3.0. More preferably, the Group VB metal phosphate possesses a P/metal mole ratio no greater than about 1.3. Most preferably, the Group VB metal phosphate possesses a P/metal mole ratio in the range from about 0.02 to about 1.0. Preferably, the Group VB metal phosphate is a niobium phosphate, more preferably, $NbOPO_4$ or the hydrated forms of $NbOPO_4$.

The Group VB metal phosphate catalysts are relatively easy to prepare. The preparations are described in *Comprehensive Inorganic Chemistry*, op. cit., pp. 612-613, and the references cited therein. Preferably, the Group VB metal phosphate catalyst is prepared by reacting a catalyst precursor compound containing a Group VB metal with a phosphorus-containing compound, such as phosphoric acid, under conditions sufficient to generate the Group VB metal phosphate. Typical catalyst precursor compounds which can be employed as starting materials include Group VB metal oxides, hydrated oxides, halides, alkoxides, and carboxylic acid salts. Anhydrous or aqueous phosphoric acid can be employed as the phosphorus-containing compound, as can chlorinated or fluorinated phosphoric acids, or chlorinated or fluorinated phosphorus-containing organic compounds. If phosphoric acid is employed, it is typically employed as an 85 weight percent aqueous solution; however, additional water can be used to obtain Group VB metal phosphate compounds having higher surface area. More specifically, the catalyst precursor, such as a Group VB metal oxide, is heated with phosphoric acid at about atmospheric pressure and at a temperature in the range from about 130° C. to about 200° C. The weight ratio of phosphoric acid to precursor compound is preferably in the range from about 5 to about 20, more preferably, in the range from about 7 to about 15, most preferably, about 10. The length of time the precursor compound and phosphoric acid are heated varies depending upon the quantity of precursor compound employed and quantity of by-products which are driven off during heating. Typically, the mixture is heated for about one to two hours; however, longer times may be employed. Afterwards, the heated mixture which comprises a liquid phase and a solid phase is cooled. The liquid is decanted from the solid, and the solid is washed with water and filtered. The washing and filtering may be repeated several times to ensure the removal of excess acid and unwanted ions. The filtered solid is dried at a temperature in the range from about 80° C. to about 150° C. in air for a time in the range from about 2 hours to about 50 hours to yield the Group VB metal phosphate. Typically, the metal phosphate compound is heat treated or calcined prior to use. Preferably, the calcination is conducted at a temperature in the range from about 200° C. to about 1000° C. for a time in the range from about 2 hours to about 50 hours. More preferably, the calcination is conducted at a temperature in the range from about 250° C. to about 800° C., most preferably, from about 300° C. to about 600° C.

C. Silicates of Groups IIA, IIIB, IVB and VB

In accordance with the process of this invention, the reforming reaction can be conducted in the presence of a catalyst comprising a metal silicate. The metal silicate is any silicate of Groups IIA, IIIB, IVB or VB of the Periodic Table. The Group IIA metals are known to include beryllium, magnesium, calcium, strontium, barium and radium. The Group IIIB metals are known to include scandium, yttrium, lanthanum and actinium.

The IVB metals include titanium, hafnium and zirconium; the VB metals include vanadium, niobium and tantalum. Preferably, the metal of the metal silicate is beryllium, magnesium, scandium, yttrium, lanthanum, titanium or zirconium. More preferably, the metal of the metal silicate is magnesium, lanthanum, yttrium, titanium or vanadium. Most preferably, the metal of the metal silicate is magnesium or yttrium or mixtures of magnesium and vanadium. The metal silicate can be employed in an amorphous form containing a distribution of silicate anions of various sizes. Alternatively, the metal silicate can be employed in a crystalline form, such as the siliceous zeolite structure exhibited by sodium magnesium silicate.

It is required that the metal silicate catalyst employed in the process of this invention be essentially free of aluminum. The term "essentially free of aluminum" means that the metal silicate contains less than about 5 weight percent aluminum. Preferably, the metal silicate contains less than about 2 weight percent aluminum, more preferably, less than about 1 weight percent aluminum.

The mole ratio of silicon to metal will vary in the metal silicate depending upon the metal cation, its valence, and the form of the silicate anion. For instance, in the case of magnesium silicate, the preferred silicon to magnesium mole ratio varies from about 0.5 to about 20. More preferably, the silicon to magnesium mole ratio varies from about 1 to about 10, most preferably, from about 1 to about 5. Other metal silicates may exhibit preferred silicon to metal mole ratios which are different from the preferred ratios shown here for magnesium silicate.

The common metal silicate catalysts which are employed in the process of this invention, such as the magnesium, titanium, and zirconium silicates, are commercially available. The less common silicates, such as the yttrium and lanthanium silicates, may be prepared by methods reported in *The Colloid Chemistry of Silica and Silicates* by Ralph K. Iler, Cornell University Press, 1955; or in *The Chemistry of Silica: Solubility, Polymerization, Colloid and Surface Properties, and Biochemistry*, by Ralph K. Iler, John Wiley & Sons, 1979; and the references therein.

More specifically, the metal silicate catalyst can be prepared by any one of the following synthetic methods. One, for example, comprises forming a mixture of silica ($SiO_2$) with the oxide of the desired metal, and calcining the thus-formed mixture at a temperature high enough to fuse the components, thereby forming the desired metal silicate. Another method, for example, involves the hydrolysis of a mixture of a tetra(alkoxy) silicon compound, such as tetra(ethoxy)silicon, and an alkoxide of the desired metal, such as tetra(methoxy) titanium. The hydrolysis reaction yields the desired metal silicate.

Preferably, the metal silicate is prepared by direct precipitation from a mixture of two aqueous solutions. One solution contains a soluble silicate salt, such as sodium silicate, while the other solution contains a soluble salt of the desired metal. Typically, the soluble silicate salt is dissolved in a minimum amount of water, which is heated, preferably to boiling, to aid in the dissolution of the salt. Optionally, the aqueous silicate solution can be acidified with strong acid, such as nitric acid, in order to prepare larger silicate anions, such as $Si_2O_5^{2-}$ or $Si_3O_7^{2-}$ or oligomers thereof. Likewise, a soluble metal salt containing the desired metal ion is dissolved in a minimum amount of hot water to make a second solution. The soluble metal salt can be, for example, a metal nitrate, such as magnesium nitrate, calcium nitrate, lanthanum nitrate, zirconium nitrate, or the like; or a soluble metal chloride, such as yttrium chloride, titanium chloride or niobium chloride. The two solutions are mixed and a precipitate forms of the desired metal silicate catalyst. The catalyst is filtered and dried by methods well known in the art.

D. Tungsten Oxides

Tungsten oxides are also suitably employed in the reforming process of this invention. Among the preferred catalysts are binary tungsten oxide compounds or salts thereof. These binary compounds contain two types of atoms, namely tungsten and oxygen, and may have an overall neutral charge or negative charge. If negatively charged, then the tungsten oxide anion will exist as a salt with an equivalently positively charged cation. Examples of such suitable tungsten oxides include mononuclear tungsten compounds containing one tungsten atom per molecular formula, such as $WO_2$, $WO_3$, and $(NH_4)_2WO_4$, as well as multi-nuclear tungsten compounds containing a plurality of tungsten atoms per molecular formula, such as para-ammonium tungstate represented by the chemical formula $(NH_4)_{10}(W_{12}O_{41})$, and $H_2(W_6O_{19})$, $[(n-C_4H_9)_4N]_2(W_6O_{19})$, and more generally $(NR_4)_2(W_6O_{19})$ and $(NR_4)_4(W_{10}O_{32})$, wherein R is H or an alkyl moiety, preferably of up to about 12 carbon atoms. It is preferred that the tungsten ions in these catalysts be in the +4, +5, or +6 oxidation state. The preferred mononuclear tungsten oxide is $(NH_4)_2WO_4$.

In addition to the above-identified tungsten oxide catalysts, there are other types of tungsten oxide compounds which are suitable for the process of this invention. These additional tungsten oxides are multinuclear clusters wherein some of the tungsten atoms have been replaced by vanadium (V), niobium (Nb), or tantalum (Ta). Accordingly, the preferred multinuclear tungsten oxide compounds can be represented by the general formula:

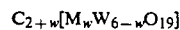

$$C_{2+w}[M_wW_{6-w}O_{19}]$$

wherein C is a monovalent cation, such as $Na^+$, $K^+$, $H^+$, or a quaternary ammonium salt $NR_4^+$, wherein R is H or an alkyl moiety of $C_1$-$C_{12}$ carbon atoms, w is an integer from 0 to 3, and M is vanadium (V), niobium (Nb), or tantalum (Ta). Preferably, C is tetrabutylammonium (+1).

The more common of the tungsten oxides, such as $WO_2$, $WO_3$, $(NH_4)_2WO_4$, and para-ammonium tungstate can be purchased commercially from Alfa Products or Aldrich Chemical Company. The less common oxides and cluster compounds can be prepared by methods described in Comprehensive Inorganic Chemistry, Vol. 3, J. C. Bailar, Jr., H. J. Emeleus, R. Nyholm, and A. F. Trotman-Dickenson, eds., Pergamon Press Ltd., Oxford (1973) pp. 763-769; and in "Isopolytungstates," by D. L. Kepert in Progress in Inorganic Chemistry, Vols. 4, Intersciences Press, New York (1962) p. 199. The preparation of $[(n-C_4H_9)_4N]_2(W_6O_{19})$ and various polyoxometalates is reported by M. Filowitz, R. K. C. Ho, W. G. Klemperer, and W. Shum in Inorganic Chemistry, 18, no.1, 93-103 (1979), and by V. W. Day, W. G. Klemperer, and C. Schwartz in the Journal of the American Chemical Society, 109, No. 20, 6030-6044 (1987).

As noted hereinbefore, it is required that the aforementioned metal silicate catalysts employed in the process of this invention be essentially free of aluminum. Preferably, the tungsten oxide catalysts of this invention are also essentially free of aluminum. The term "essentially free of aluminum" means that the catalyst contains less than about 5 weight percent aluminum. Preferably, the catalyst contains less than about 2 weight percent aluminum, more preferably, less than about about 1 weight percent aluminum. It is believed that the presence of aluminum enhances the formation of undesirable cracking products and dehydrogenation products; however, such a theory should not be limiting of the process of this invention.

It is additionally preferred that the above-identified catalysts be essentially free of hydrogenation metals. In this instance, the phrase "essentially free of hydrogenation metals" means that the concentration of a hydrogenation metal in the catalyst is less than about 0.1 weight percent, preferably, less than about 0.01 weight percent. For the purposes of this invention, a "hydrogenation metal" is one which is capable of removing hydrogen from the reactant alkyleneamines and thereby catalyzing their reductive reformation to product alkyleneamines different from the reactants. The hydrogenation metals are known in the prior art to include zerovalent metals of Group VIII, namely iron, cobalt, nickel, ruthenium, rhodium, palladium, osmium, iridium and platinum, as well as zerovalent copper, chromium, molybdenum and the like, as disclosed in U.S. Pat. No. 4,625,030 and U.S. Pat. No. 4,568,746. Frequently, these metals are provided in the reductive reformation catalyst as the oxides, which are thereafter reduced to zerovalent metal by hydrogen present in the reductive reformation process.

It is preferred that the aforementioned catalysts (A-D) be insoluble in the reforming reaction mixture, thereby acting as heterogeneous catalysts. Optionally, any of the catalysts can be made more insoluble by (a) deposition onto a support material, or (b) binding with a refractory metal oxide or a support precursor. Any support or binder material is acceptable provided that it does not enhance the formation of undesirable internal cyclization products, dehydrogenation products or cracking products in the process of this invention. Suitable supports or binders include carbon and any refractory oxide, such as alumina (except as noted hereinabove wherein alumina may not be present in significant concentration), silica, zirconia, thoria, magnesia, titania, kielselguhr, and mixtures of these materials. Suitable support precursors include hydrated metal oxides and metal alkoxides. Preferably, the support or binder material is silica or titania. The support material typically has a surface area of at least about 0.1 m²/g. Preferably, the support material has a surface area in the range from about 5 m²/g to about 600 m²/g, most preferably in the range from about 50 m²/g to about 200 m²/g. These surface areas are measured by the Brunauer-Emmett-Teller (BET) method, as described by R. B. Anderson, in Experimental Methods in Catalytic Research, Academic Press (1968) pp. 48-66.

The catalyst compounds can be deposited onto the support material in any known fashion, such as by impregnation or by precipitation in situ from the catalyst preparation reaction. In these types of preparation the catalyst is adsorbed onto the support. Alternatively, the catalyst can be chemically reacted onto the support. In this method a catalyst precursor compound is reacted with the hydroxyl functionalities of the support to yield a catalyst precursor chemically bound to the support. For example, niobium chloride reacts with the hydroxyl moieties of silica to yield niobium chloride bound through an oxygen to silicon. The bound catalyst precursor can then be converted into the oxide catalyst of this invention by hydrolysis or heating. Similarly, the bound catalyst precursor can be converted into the phosphate catalyst of this invention by reaction with phosphoric acid. For example, the Group VB metal chloride bound to silica, described hereinabove, can be treated with an excess of 85 weight percent phosphoric acid at a temperature in the range from about 130° C. to about 200° C. for a time in the range from about 1 hour to about 5 hours to yield a Group VB metal phosphate bound to silica.

The amount of catalyst, which is employed in the process of this invention, is any amount which is effective in producing the desired amine-extended cyclic alkyleneamine products. The amount of catalyst varies widely depending upon the specific reactants and process conditions employed. Typically, for a batch reaction the quantity of catalyst is in the range from about 0.1 weight percent to about 20 weight percent based on the weight of reactant cyclic alkyleneamine. Preferably, the amount of catalyst is in the range from about 1 weight percent to about 15 weight percent based on the weight of reactant cyclic alkyleneamine.

The process of this invention can be conducted in any suitable reactor, including batch reactors, continuous fixed-bed reactors, slurry reactors, fluidized bed reactors, and catalytic distillation reactors. Preferably, the reactor is a continuous fixed-bed reactor.

The feedstream comprising the cyclic alkyleneamine or mixture of cyclic alkyleneamines, and optional solvent and/or acyclic alkylamine, is contacted with the catalyst at any operable temperature which promotes the reforming reaction and produces the desired amine-extended cyclic alkyleneamine products. Typically, the temperature is maintained below about 350° C. Preferably, the temperature is in the range from about 175° C. to about 325° C. More preferably, the temperature is in the range from about 175° C. to about 300° C. Most preferably, the temperature is in the range from about 200° C. to about 300° C. Below the preferred lower temperature the conversion of cyclic alkyleneamine reactant may be low. Above the preferred upper temperature the selectivity for amine-extended cyclic alkyleneamines may decrease, and increasing yields of cracking products, dehydrogenation products and internal cyclization products may be obtained.

Likewise, the cyclic alkyleneamine or mixture of cyclic alkyleneamines is contacted with the catalyst at any operable pressure which promotes the reforming reaction and produces the desired amine-extended cyclic alkyleneamine products. Preferably, the pressure is sufficient to maintain the reactants in the liquid state at the temperature of the reaction. More preferably, the pressure is in the range from about 25 psig to about 4000 psig. Even more preferably, the pressure is in the range from about 500 psig to about 3000 Psig. most preferably, the pressure is in the range from about 1000 psig to about 2000 psig. In batch reactors the pressure is autogenous, and depends upon the vapor pressures of the reactants and products and the temperature of the reaction.

When the process of this invention is conducted in a continuous flow reactor, the flow rate of the reactants can be varied. Generally, the cyclic alkyleneamine or mixture of cyclic alkyleneamines is premixed with the optional acyclic alkylamine and/or solvent to form a feedstream which is fed into the reactor at any operable flow rate which allows for reaction to predominantly amine-extended cyclic alkyleneamine products. The flow rate is expressed as the liquid hourly space velocity and is given in units of grams of total reactants per milliliter of total reactor volume per hour, $g\ ml^{-1}\ hr^{-1}$. It is preferred to employ a liquid hourly space velocity in the range from about $0.1\ g\ ml^{-1}\ hr^{-1}$ to about $10.0\ g\ ml^{-1}\ hr^{-1}$; more preferably in the range from about $0.5\ g\ ml^{-1}\ hr^{-1}$ to about $4.0\ g\ ml^{-1}\ hr^{-1}$. It is understood that the liquid hourly space velocity controls the residence time of the reactants in the continuous flow reactor.

When the process of this invention is conducted in a batch reactor, the reaction time determines the length of contact between the reactants and the catalyst. Any reaction time which yields the desired amine-extended cyclic alkyleneamine products is acceptable. The reaction time depends upon the quantity of reactants, the quantity of catalyst, the temperature of the reaction and desired degree of conversion. Preferably, the reaction time in a batch reactor is in the range from about 1 hour to about 20 hours.

When the cyclic alkyleneamine reactant is contacted with itself or with any other cyclic alkyleneamine or acyclic alkylamine reactant in the presence of one of the catalysts described hereinbefore, the cyclic alkyleneamine is reformed into at least one amine-extended cyclic alkyleneamine product. Generally, a mixture of such products is obtained. In addition, ammonia is eliminated as a by-product. Typically, the molecular weight of the products is greater than the molecular weight of the reactant(s). Preferably, the product is a mixture of amine-extended cyclic alkyleneamines enriched in linearly-extended homologues. For example, if the reactant is piperazine or piperidine, the preferred amine-extended cyclic alkyleneamines are 1,2-bis(piperazinyl)ethane and N,N'-bis(piperidinyl)pentane, respectively. If the reactants are a mixture of piperazine and ethylenediamine, the preferred amine-extended cyclic alkyleneamine is also N-(2-aminoethyl)piperazine. If the reactants are a mixture of piperazine and N-(2-aminoethyl)piperazine, the preferred product is 1,2-bis(piperazinyl)ethane. In addition to these preferred linearly-extended products, lesser amounts of undesirable cracking products and cyclic products may be formed. The undesirable cyclic products contain new N-heterocycles, such as 1,4-diaza-[2.2.2]bicyclooctane, formed through internal cyclization of one of the reactants. Dehydrogenation products, such as pyrazines, typically do not form in significant quantities in the process of this invention.

The preferred amine-extended cyclic alkyleneamine products can be represented by the following formula:

$C_1$–$C_{12}$ carbon atoms such as methyl, ethyl or propyl, or an aminoalkyl moiety of $C_1$–$C_{12}$ carbon atoms; each y is independently an integer from 0 to about 12; each z is independently an integer from 1 to 3; each l is independently an integer from 0 to about 6; and j' is an integer from 0 to about 6. Some examples of products which satisfy this formula include N-(2-aminoethyl) piperazine, bis(piperazinyl)alkanes and analogous higher molecular weight oligomers. Preferably, R is hydrogen. More preferably, R is hydrogen, y is 0 to 2, z is 2, j' is 1 or 2, and each l is independently 0 to 2. Most preferably, the products are N-(2-aminoethyl)piperazine, 1,2-bis(piperazinyl)-ethane, and/or N,N'-bis(2-piperazinylethyl)-piperazine.

For the purposes of this invention "conversion" is defined as the total weight percentage of cyclic alkyleneamine(s) and optional acyclic alkylamine reactants lost as a result of reaction. The conversion varies widely depending upon the reactants, the form of the catalyst, and the process conditions, such as temperature, pressure, and flow rate. Within the preferred temperature range, as the temperature increases the conversion generally increases. Within the preferred space velocity range, as the space velocity increases the conversion generally decreases. Typically, the conversion is at least about 2 weight percent. Preferably, the conversion is at least about 5 weight percent; more preferably at least about 10 weight percent; even more preferably, at least about 20 weight percent; and most preferably, at least about 35 weight percent.

Likewise, for the purposes of this invention "selectivity" is defined as the weight percentage of converted reactants which form a particular amine-extended cyclic alkyleneamine product. Typically, the selectivities also vary widely depending upon the reactants, the form of the catalyst, and the process conditions. Typically, the process of this invention achieves high selectivities to amine-extended cyclic alkyleneamine products. Within the preferred temperature range as the temperature increases, the selectivity for amine-extended cyclic alkyleneamines generally decreases. Within the preferred space velocity range as the space velocity increases, the selectivity for amine-extended cyclic alkyleneamines increases. Preferably, the combined selectivity to all amine-extended cyclic alkyleneamines is at least about 45 weight percent; more preferably, at least about 60 weight percent, even more preferably, at least about 75 weight percent, and most preferably, at least about 85 weight percent.

The following examples are illustrative of the invention; but, are not intended to be limiting thereof. All percentages are given in weight percent, unless noted otherwise. The following abbreviations are used to indicate the reactants and products:

| | |
|---|---|
| EDA | ethylenediamine |
| DETA | diethylenetriamine |
| PIP | piperazine |
| AEP | N-(2-aminoethyl)piperazine |

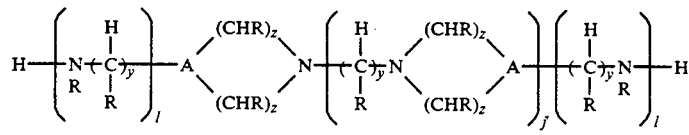

wherein each A is independently N or CH, each R is independently hydrogen, a lower alkyl moiety of

| | |
|---|---|
| DIAEP | N,N'-di(2-aminoethyl)piperazine |

| | -continued |
|---|---|
| BISPIP | 1,2-bis(piperazinyl)ethane or bispiperazine |
| PEEDA | (piperazinylethyl)ethylenediamine | nitrogen, heated to 300° C. and maintained thereat for 6 hours. After heating, the reactor is cooled and depressurized, and its contents are analyzed by gas phase chromatography with the conditions and results set forth in Table I.

TABLE I

| Ex. # | Catalyst(1) | PIP (g) initial | AEP (g) initial | Cat (g) | Hrs at 300° C. | % Conv.(2) | % Sel(2) EDA | DABCO |
|---|---|---|---|---|---|---|---|---|
| 1b | NbOPO$_4$ | 28.6 | 24.5 | 2.00 | 6 | 2.16 | 9.54 | 19.03 |
| 2b | Nb$_2$O$_5$/Boehmite | 28.6 | 24.5 | 2.00 | 6 | 5.40 | 5.89 | 7.22 |
| 3b | MgSi$_2$O$_5$ | 21.4 | 28.6 | 2.00 | 5 | 51.82 | — | 5.58 |
| 4b | MgSi$_2$O$_5$ | 28.5 | 21.5 | 2.00 | 5 | 37.87 | 2.17 | 3.97 |
| 5b | La$_2$(Si$_2$O$_5$)$_3$ | 28.5 | 26.5 | 2.00 | 5 | 9.51 | — | 12.61 |
| 6b | Y$_2$(Si$_2$O$_5$)$_3$ | 28.5 | 23.7 | 2.30 | 5 | 20.35 | 0.49 | 9.03 |
| 7b | Mg$_6$(VO$_4$)$_2$(Si$_2$O$_5$)$_3$ | 28.6 | 24.9 | 2.17 | 5 | 29.76 | 0.56 | 5.64 |
| 8b | Nb$_2$O$_5$.5SiO$_2$ | 28.6 | 24.5 | 2.00 | 3 | 8.92 | 3.06 | 6.85 |
| 9 | TiO$_2$.SiO$_2$ | 28.6 | 24.5 | 2.94 | 5 | 15.08 | 0.73 | 8.02 |
| 10b | (NH$_4$)$_2$WO$_4$/TiO$_2$ | 28.6 | 24.5 | 2.00 | 6 | 17.32 | 2.74 | 4.19 |

| Ex. # | DETA | DIAEP | PEEDA | BISPIP | AE-PEEDA | PEDETA | AEBIS-PIP | PEAEP | TRIS-PIP | Others (3) |
|---|---|---|---|---|---|---|---|---|---|---|
| 1b | — | 9.54 | 23.84 | 7.59 | 5.51 | — | — | — | — | 24.95 |
| 2b | 6.83 | 7.00 | 17.65 | 11.22 | 5.46 | 2.78 | 4.89 | 3.46 | — | 27.60 |
| 3b | — | — | 4.66 | 38.19 | — | — | 17.57 | 9.42 | 18.70 | 5.88 |
| 4b | — | — | 8.12 | 46.22 | — | — | 13.35 | 9.34 | 11.01 | 5.82 |
| 5b | — | — | 7.98 | 46.85 | — | — | 20.13 | 12.44 | — | 0 |
| 6b | — | 1.47 | 7.39 | 37.86 | 2.13 | 1.33 | 14.78 | 9.07 | 2.45 | 14.00 |
| 7b | — | 1.40 | 6.90 | 35.01 | 1.59 | 0.89 | 13.81 | 7.91 | 5.05 | 21.24 |
| 8b | 3.22 | 3.37 | 15.09 | 32.63 | 4.25 | 2.76 | 10.34 | 7.37 | — | 11.09 |
| 9 | — | 1.92 | 9.62 | 32.89 | 3.05 | 2.32 | 14.59 | 9.02 | 1.99 | 15.85 |
| 10b | 0.76 | 6.48 | 15.16 | 30.21 | 3.38 | 2.26 | 7.62 | 4.52 | — | 23.44 |

(1) Catalysts of Examples 3, 4, 6, 7, and 8 calcined at 550° C.; Catalyst of Example 5 calcined at 350° C. Catalyst of Example 9 is a commercial sample of titanium silicate TiO$_2$.SiO$_2$, 30.7 weight percent TiO$_2$.
(2) % Conversion (% Conv) is calculated by subtracting the sum of the GC area percentages for AEP and PIP from 100%. % Selectivity (% Sel) is calculated by dividing the GC area percentage for a particular species by the conversion.
(3) Others include higher oligomers and unidentified products. Pyrazines are present at less than about 1 weight percent concentration.

| AEPEEDA | N-(aminoethylpiperazinylethyl)ethylenediamine |
|---|---|
| PEDETA | (piperazinylethyl)diethylenetriamine |
| AEBISPIP | N-(2-aminoethyl)bispiperazine |
| PEAEP | (piperazinylethyl)aminoethylpiperazine |
| TRISPIP | N,N'-bis(2-piperazinylethyl)piperazine or trispiperazine |
| DABCO | 1,4-diazabicyclo-[2.2.2]-octane |

EXAMPLE 1

(a) Preparation of Niobium Phosphate Catalyst

Niobic acid, Nb$_2$O$_5$.xH$_2$O (60.0 g) is stirred in 85 percent phosphoric acid (600.0 g) at 150° C. The niobium oxide dissolves to form a solution, and upon further heating a precipitate forms. The precipitate is boiled in the phosphoric acid solution for about 2 hours with stirring. The mixture is cooled to room temperature, and the liquid is decanted from the precipitate. Water (500 ml) is added to the precipitate with stirring, and the precipitate is filtered. The washing and filtering cycle is repeated three times. The filtered solid is dried at 150° C. under air, then heated overnight at 300° C. to yield a niobium phosphate catalyst. The elemental analysis of the catalyst is consistent with the composition NbOPO$_4$.

(b) Reforming a Mixture of AEP and PIP

The catalyst prepared hereinabove is employed to reform a mixture of piperazine and N-(2-aminoethyl)piperazine according to the following general procedure. The catalyst and amine reactants are loaded into a batch reactor equipped with a pressure gauge and temperature sensor. The reactor is sealed, flushed with nitrogen, heated to 300° C. and maintained thereat for 6 hours. After heating, the reactor is cooled and depressurized, and its contents are analyzed by gas phase chromatography with the conditions and results set forth in Table I.

It is seen that niobium phosphate catalyzes the reforming of a mixture of piperazine and aminoethylpiperazine predominantly to amine-extended cyclic alkyleneamines.

EXAMPLE 2

(a) Preparation of Niobic Oxide Catalyst

Niobic Acid, Nb$_2$O$_5$.xH$_2$O (23.0 g, Niobium Products Corp., CBMM number AD 222) and boehmite alumina (23.0 g) are mixed and pressed at 20,000 psi into cylindrical pellets 1 inch in diameter by 1 inch in length. Each pellet contains approximately 25 grams niobic acid. The pressed pellets are dried at 120° C. for 4 hours. The dried pellets are heated slowly under air to a temperature of 300° C. and calcined overnight at that temperature. The catalyst pellets are crushed and sieved to 14–20 mesh prior to use in the reactor.

(b) Reforming a Mixture of PIP and AEP

The catalyst prepared hereinabove is employed in reforming a mixture of piperazine and N-(2-aminoethyl)piperzine according to the procedure of Example 1b with the conditions and results set forth in Table I. It is seen that niobium oxide catalyzes the reforming of this mixture predominantly to amine-extended cyclic alkyleneamines.

EXAMPLES 3–9

(a) Preparation of Catalysts

A series of metal silicate catalysts are prepared according to the following general procedure: Na$_2$SiO$_3$.9H$_2$O is dissolved in 1200 ml of water and heated to 80°

C. Concentrated nitric acid is slowly added to the solution so that no precipitate forms during the addition. The acidified silicate solution is heated to boiling and the volume is raised to 2000 ml with water. In a separate flask a soluble metal salt, typically the chloride or nitrate, is dissolved in 2000 ml of water and heated to boiling. The acidified silicate solution is added hot at a rate of 100 ml/min to the nitrate solution with rapid stirring. A precipitate forms. The supernatent and the precipitate are heated and stirred for about 3 hours at boiling, then cooled overnight at room temperature. The cooled mixture is filtered, and the precipitate is washed with about 2000 ml of water and refiltered. The washing procedure is repeated twice more, and the resulting filtercake is dried at 100° C. overnight. The dried filtercake is calcined under air at 550° C. over a second night to yield a metal silicate catalyst, which is employed in the reforming process of this invention. Table II lists the kind and quantity of soluble metal salt, the quantities of nitric acid and sodium silicate, and the approximate formula of the resulting metal silicate catalyst.

TABLE II

| EX. | Metal Salt (g) | $Na_2SiO_3 \cdot 9H_2O$ (g) | $HNO_3$ (ml) | Approx. Formula |
| --- | --- | --- | --- | --- |
| 3a | $Mg(NO_3)_2 \cdot 6H_2O$ (100.0) | 222.5 | 49 | $MgSi_2O_5$ |
| 4a | $Mg(NO_3)_2 \cdot 6H_2O$ (200.2) | 445.1 | 98 | $MgSi_2O_5$ |
| 5a | $La(NO_3)_3 \cdot 6H_2O$ (108.3) | 213.2 | 49 | $La_2(Si_2O_5)_3$ |
| 6a | $YCl_3 \cdot 6H_2O$ (53.4) | 150.4 | 33 | $Y_2(Si_2O_5)_3$ |
| 7a | $Mg(NO_3)_2 \cdot 6H_2O$ (76.2 g) | 83.4① | 19 | $Mg_6(VO_4)_2(Si_2O_5)_3$ |
| 8a | $NbCl_5$ (76.0) | 200.0 | 0 | $Nb_2O_5 \cdot 5SiO_2$ |

①Silicate solution additionally contains $Na_3VO_4$ (18.1 g).

(b) Reforming of a Mixture of PIP and AEP

Piperazine, aminoethylpiperazine and a silicate catalyst, prepared hereinabove or obtained commercially, are placed in a batch reactor equipped with a pressure gauge and a temperature sensor. The reactor is sealed, flushed with nitrogen, heated to 300° C., and maintained thereat for 5 hours. The quantities of reactants, process conditions and results are set forth in Table I. It is seen that metal silicates from Groups IIA, IIIB, IVB and VB catalyze the reforming of a mixture of piperazine and aminoethylpiperazine to a mixture of predominantly amine-extended piperazines, such as N,N'-bis(-piperazinyl)ethane and aminoethylbispiperazinyl) ethane.

EXAMPLE 10

(a) Preparation of Titania-Supported Ammonium Tungstate

Ammonium tungstate (15 g; Amends Chemical Company) is added to 400 ml of water to which 5 ml of 30 percent hydrogen peroxide are added. The resulting mixture is heated with stirring at 80° C.-90° C. for 60 minutes to form a solution. The solution is cooled to room temperature and added to a flask containing titania (25 g). Water is removed from the mixture by rotary evaporation. The resulting solid is dried in a muffle furnace at 350° C. overnight to form a titania-supported tungsten oxide catalyst.

(b) Reforming of a Mixture of PIP and AEP

The catalyst prepared hereinabove is employed in reforming a mixture of piperazine and N-(2-aminoethyl)-piperazine according to the procedure described in Example 1. Process conditions and results are set forth in Table I. It is seen that ammonium tungstate catalyzes the reforming of a mixture of piperazine and aminoethylpiperazine to predominantly amine-extended cyclic alkyleneamines.

EXAMPLE 11

The magnesium silicate catalyst of Example 3(a) (1.1 g) and piperazine (30.5 g) are loaded into a batch reactor and heated at 300° C. for a total of 9 hours. The contents are cooled and analyzed with the following results: conversion of PIP, 35 percent; selectivity to BISPIP, 30.0 percent; PEEDA, 14.2 percent; AEP, 8.7 percent; PEAEP, 12.6 percent; AEBISPIP, 2.4 percent; and TRISPIP, 4.5 percent. Pyrazine is identified at levels less than 1 weight percent. It is seen that magnesium silicate catalyzes the reformation of piperazine to amine-extended piperazines, predominantly N,N'-bis(-piperazinyl)ethane.

EXAMPLE 12

The magnesium silicate catalyst of Example 3(a) (1.0 g) and piperidine (30.5 g) are loaded into a batch reactor and heated at 300° C. for a total of 9 hours. The contents are cooled and analyzed with the following results: conversion of piperidine, 22 percent; selectivity to N,N'-bis(piperidinyl)pentane, 67.4 percent, and N-aminopentylpiperidine, 13.6 percent. It is seen that magnesium silicate catalyzes the reformation of piperidine to amine-extended piperidines, predominantly N,N'-bis(piperidinyl)pentane.

EXAMPLE 13

The magnesium silicate catalyst of Example 3(a) (1.0 g), piperazine (29.5 g) and ethylenediamine (26.3 g) are loaded into a batch reactor and heated to 300° C. for a total of 4.5 hours. The contents are cooled and analyzed with the following results: total conversion of reactants, 9 percent; selectivity to AEP, 53 percent; PEEDA, 24 percent; and BISPIP, 5 percent. It is seen that magnesium silicate catalyzes the reforming of a mixture of piperazine and ethylenediamine to aminoethyl-extended piperazines, predominantly N-(2-aminoethyl)piperazine.

EXAMPLE 14

Niobic acid supported on boehmite alumina (5.0 g), prepared as in Example 2, is employed in reforming pyrrolidine (100 ml) according to the procedure described in Example 1 with the exception that the total reaction time is 325 min with about 200 min at 270°-280° C. The remaining reaction time is spent heating the sample to 270° C. The following results are obtained: Conversion of pyrrolidine, 5 percent; Selectivity to N-(4-aminobutyl)pyrrolidine, 59 percent. It is seen that niobium oxide catalyzes the reforming of pyrrolidine to predominantly an aminoalkyl-extended pyrrolidine.

What is claimed is:

1. A process of reforming cyclic alkyleneamines or aminoalkyl-substituted cyclic alkyleneamines comprising contacting in the liquid phase and in the absence of reactive alcohols a cyclic alkyleneamine, an aminoalkyl-substituted cyclic alkyleneamine, or a mixture thereof with a catalyst under reaction conditions such that a mixture of amine-extended cyclic alkyleneamines or amine-extended aminoalkyl-substituted cyclic alkyleneamines is formed in a combined selectivity of at least about 45 weight percent, the catalyst being selected from the group consisting of:
   (a) Group VB metal oxides;
   (b) Group VB metal phosphates;
   (c) silicates of Groups IIA, IIIB, IVB, and VB, with the proviso that the metal silicate is essentially free of aluminum; and
   (d) binary compounds of tungsten and oxygen and salts thereof, and binary compounds of tungsten and oxygen wherein a portion of the tungsten atoms are replaced by vanadium, niobium, or tantalum.

2. The process of claim 1 wherein the cyclic alkyleneamine reactant is represented by the formula:

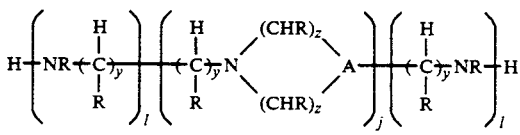

wherein A is either N or CH, each R is independently hydrogen, an alkyl moiety Of $C_1$–$C_{12}$ carbon atoms; or an aminoalkyl moiety of $C_1$–$C_{12}$ carbon atoms; each y is independently an integer from 0 to about 12; each z is independently an integer from 1 to 3; each l is independently an integer from 0 to about 6; and j is an integer from 1 to about 6.

3. The process of claim 2 wherein the cyclic alkyleneamine reactant is piperazine.

4. The process of claim 2 wherein the cyclic alkyleneamine reactant is piperidine.

5. The process of claim 2 wherein the cyclic alkyleneamine reactant is N-(2-aminoethyl)piperazine.

6. The process of claim 2 wherein the cyclic alkyleneamine reactant is pyrrolidine.

7. The process of claim 1 wherein the cyclic alkyleneamine reactant is a mixture of piperazine and N-(2-aminoethyl)piperazine.

8. The process of claim 1 wherein an acyclic alkylamine is present in the reactant feedstream.

9. The process of claim 1 wherein the catalyst is a Group VB metal phosphate.

10. The process of claim 9 wherein the metal of the metal phosphate is niobium.

11. The process of claim 10 wherein the metal phosphate is $NbOPO_4$.

12. The process of claim 1 wherein the catalyst is a Group VB metal oxide.

13. The process of claim 12 wherein the catalyst is an oxide or hydrated oxide of niobium.

14. The process of claim 1 wherein the catalyst is a binary compound of tungsten and oxygen or salt thereof, or a binary compound of tungsten and oxygen wherein a portion of the tungsten atoms are replaced by vanadium, niobium or tantalum.

15. The process of claim 14 wherein the catalyst is $(NH_4)_2WO_4$.

16. The process of claim 14 wherein the catalyst is represented by the formula:

wherein C is a monovalent cation, w is an integer from 0 to 3, and M is vanadium (V), niobium (Nb), or tantalum (Ta).

17. The process of claim 1 wherein the catalyst is a metal silicate wherein the metal is selected from the group consisting of the metals of Groups IIA, IIIB, IVB and VB.

18. The process of claim 17 wherein the catalyst is magnesium silicate.

19. The process of claim 17 wherein the catalyst is lanthanum silicate or yttrium silicate.

20. The process of claim 17 wherein the silicate is titanium silicate.

21. The process of claim 17 wherein the catalyst is niobium silicate.

22. The process of claim 1 wherein the quantity of catalyst is in the range from about 0.1 weight percent to about 20 weight percent based on the weight of the cyclic alkyleneamine reactant.

23. The process of claim 1 wherein the temperature is in the range from about 175° C. to about 325° C.

24. The process of claim 23 wherein the temperature is in the range from about 175° C. to about 300° C.

25. The process of claim 1 wherein the pressure is in the range from about 25 psig to about 4000 psig.

26. The process of claim 1 wherein the liquid hourly space velocity is in the range from about 0.1 g ml$^{-1}$ hr$^{-1}$ to about 10.0 g ml$^{-1}$ hr$^{-1}$.

27. The process of claim 1 wherein the amine-extended cyclic alkyleneamine product is represented by the formula:

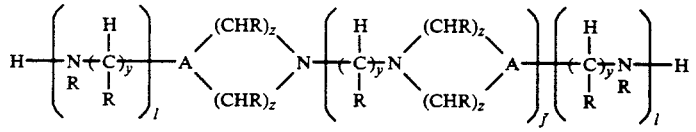

wherein each A is independently CH or N; each R is independently hydrogen, a lower alkyl moiety of $C_1$–$C_{12}$ carbon atoms, or an aminoalkyl moiety of $C_1$–$C_{12}$ carbon atoms; each y is independently an integer from 0 to about 12; each z is independently an integer from 1 to 3; each l is independently an integer from 0 to about 6; and j' is an integer from 0 to about 6.

28. The process of claim 27 wherein the amine-extended cyclic alkyleneamine is N-(2-aminoethyl)piperazine, N,N'-bis(piperazinyl)-ethane, or tris(piperazinyl)ethane.

29. The process of claim 1 wherein the combined selectivity for amine-extended cyclic alkyleneamines is at least about 60 weight percent.

30. A process of reforming piperazine or a mixture of piperazine and aminoethylpiperazine comprising contacting piperazine, and optionally aminoethylpiperazine, in the liquid phase and in the absence of reactive alcohols with a catalyst of magnesium silicate or niobium oxide at a temperature in the range from about 200° C. to about 325° C. and a pressure in the range from about 500 psig to about 3000 psig such that a mixture of amine-extended piperazines is formed containing 1,2-bispiperazinyl-ethane and N,N'-bis(2-piperazinyethyl)piperazine.

* * * * *

UNITED STATES PATENT AND TRADEMARK OFFICE
CERTIFICATE OF CORRECTION

PATENT NO. : 5,256,786

DATED : October 26, 1993

INVENTOR(S) : Bowman, et al.

It is certified that error appears in the above-identified patent and that said Letters Patent is hereby corrected as shown below:

Column 17, line 2, "aminoalkyl-substituted cyclic alkyleneamines comprising", should correctly read, --aminoalkyl-substituted cyclic alkyleneamines, wherein the cyclic alkyleneamine is characterized as a saturated heterocycle containing one or two nitrogen atoms, the process comprising--.

Signed and Sealed this

Twenty-eighth Day of November 1995

Attest:

Attesting Officer

BRUCE LEHMAN

Commissioner of Patents and Trademarks